United States Patent [19]

Lederis et al.

[11] Patent Number: 4,533,654

[45] Date of Patent: Aug. 6, 1985

[54] UROTENSIN PEPTIDES

[75] Inventors: Karl P. Lederis; Keith L. MacCannell, both of Calgary, Canada; Tomoyuki Ichikawa, Tokyo, Japan

[73] Assignee: The Salk Institute For Biological Studies, San Diego, Calif.

[21] Appl. No.: 600,554

[22] PCT Filed: Sep. 29, 1982

[86] PCT No.: PCT/US82/01349

§ 371 Date: Apr. 3, 1984

§ 102(e) Date: Apr. 6, 1984

[87] PCT Pub. No.: WO84/01378

PCT Pub. Date: Apr. 12, 1984

[51] Int. Cl.$^3$ .................. A61K 37/00; C07C 103/52
[52] U.S. Cl. ........................................ 514/12; 514/13; 260/112.5 R
[58] Field of Search ............... 260/112.5 R; 424/177; 514/12, 13

[56] References Cited

U.S. PATENT DOCUMENTS 4,385,050  5/1983  Lederis et al. .................. 424/177

OTHER PUBLICATIONS

Program and Abstracts, Jun. 1982, Meeting of the Endocrine Society—Abstract No. 756 (p. 268).
Rivier et al., Biopolymers 17, (1978), 1927–1938.
Gerriston et al., European Journal of Pharmacology 60, (1979), 211–220.
Akaji et al., Chem. Pharmacology Bulletin 30, 349–353 (1982).
Kapoor, Journal of Pharmaceutical Science 59, (1970), 1–27.
Clark et al., Biol. Abstr. 74, (1982), 70624.
Vale et al., Science 213, (1981), 1394–1397.
Atherton et al., Bioorganic Chem. 8, (1979), 351–370.
Melchorri et al., Regulatory Peptides 2, (1981), 1–13.
Schröeder et al., The Peptides 1, (1965), 72–75.
Merrifield, Solid Phase Peptide Synthesis (1963), 2149–2154.

*Primary Examiner*—Delbert R. Phillips
*Attorney, Agent, or Firm*—Fitch, Even, Tabin & Flannery

[57] ABSTRACT

UI (Urotensin I) or carp urotensin, obtained from *Cyprinus carpio*, has the formula: H-Asn-Asp-Asp-Pro-Pro-Ile-Ser-Ile-Asp-Leu-Thr-Phe-His-Leu-Leu-Arg-Asn-Met-Ile-Glu-Met-Ala-Arg-Asn-Glu-Asn-Gln-Arg-Glu-Gln-Ala-Gly-Leu-Asn-Arg-Lys-Tyr-Leu-Asp-Glu-Val-NH$_2$. UI or a biologically active fragment thereof or a pharmaceutically acceptable salt of either, dispersed in a pharmaceutically acceptable liquid or solid carrier, can be administered to mammals to achieve a substantial elevation of ACTH, $\beta$-endorphin, $\beta$-lipotropin and corticosterone levels and/or a lowering of systemic blood pressure over an extended period of time.

9 Claims, No Drawings

UROTENSIN PEPTIDES

This invention was made with Government support under Grant No. AM-26741 awarded by the National Institutes of Health. The Government has certain rights in this invention.

This invention is directed to peptides related to Urotensin I (UI) from carp and to methods for pharmaceutical treatment of mammals using such peptides. More specifically, the invention relates to UI and fragments of UI, to pharmaceutical compositions containing UI or fragments thereof, and to methods of treatment of mammals using such compositions.

BACKGROUND OF THE INVENTION

Experimental and clinical observations have supported the concept that the hypothalamus plays a key role in the regulation of adenohypophysial corticotropic cells' secretory functions. Over 25 years ago, Guillemin, Rosenberg and Saffran and Schally independently demonstrated the presence of factors in hypothalamus which would increase the rate of ACTH secretion by the pituitary gland incubated in vitro or maintained in an organ culture. A physiologic corticotrop regulatory factor, CRF, was extracted from sheep hypothalamic fragments and characterized and synthesized by the Peptide Biology Laboratory at The Salk Institute, as described in Vale et al., *Science* 213: 1394–1397, 1981.

Sauvagine is a 40-residue, amidated generally similar peptide, which was isolated from the skin of the South American frog *Phyllomedusa sauvagei* and which was characterized by Erspamer et al. and described in *Regulatory Peptides*, Vol. 2 (1981), pp. 1–13. Sauvagine has the formula: pGlu-Gly-Pro-Pro-Ile-Ser-Ile-Asp-Leu-Ser-Leu-Glu-Leu-Leu-Arg-Lys-Met-Ile-Glu-Ile-Glu-Lys-Gln-Glu-Lys-Glu-Lys-Gln-Gln-Ala-Ala-Asn-Asn-Arg-Leu-Leu-Leu-Asp-Thr-Ile-$NH_2$. Sauvagine has been reported to have biological activity in lowering blood pressure in mammals and in stimulating the secretion of ACTH and $\beta$-endorphin.

SUMMARY OF THE INVENTION

UI from *Cyprinus carpio* has now been isolated, purified, characterized and synthesized. It is a polypeptide having the formula: H-Asn-Asp-Asp-Pro-Pro-Ile-Ser-Ile-Asp-Leu-Thr-Phe-His-Leu-Leu-Arg-Asn-Met-Ile-Glu-Met-Ala-Arg-Asn-Glu-Asn-Gln-Arg-Glu-Gln-Ala-Gly-Leu-Asn-Arg-Lys-Tyr-Leu-Asp-Glu-Val-$NH_2$, and may alternatively be referred to as carp urotensin. UI has been found to stimulate ACTH and $\beta$-endorphin activities in vitro and in vivo and to lower blood pressure for an extended time period. UI in substantially pure form (i.e. substantially free of the remainder of a crude biological extract or of related synthetic replicates) can be employed in pharmaceutical compositions, and a purity of at least about 93% or higher (based upon other peptides present) is practically obtainable and preferred for clinical testing.

The fragment of carp urotensin (UI 4-41) having the following formula: H-Pro-Pro-Ile-Ser-Ile-Asp-Leu-Thr-Phe-His-Leu-Leu-Arg-Asn-Met-Ile-Glu-Met-Ala-Arg-Asn-Glu-Asn-Gln-Arg-Glu-Gln-Ala-Gly-Leu-Asn-Arg-Lys-Tyr-Leu-Asp-Glu-Val-$NH_2$ has substantially the same biological activity as the 41-residue polypeptide.

Pharmaceutical compositions in accordance with the invention include synthetic UI or its fragments, or nontoxic addition salts thereof, dispersed in a pharmaceutically acceptable liquid or solid carrier. The administration of such peptides or pharmaceutically acceptable addition salts thereof to mammals in accordance with the invention may be carried out for the regulation of secretion of ACTH, $\beta$-endorphin, $\beta$-lipotropin, and corticosterone and/or for the long-lasting lowering of systemic blood pressure and related cardiovascular effects.

DETAILED DESCRIPTION OF THE PREFERRED EMBODIMENTS

UI was isolated from carp urophysis extracts, purified and characterized; urophyses are the hormone storage-release organs of the caudal neurosecretory system. The nomenclature used to define the peptides is that specified by Schroder and Lubke, "The Peptides", Academic Press (1965) wherein, in accordance with conventional representation, the N-terminal appears to the left and the C-terminal to the right. Where the amino acid residue has isomeric forms, it is the L-form of the amino acid that is represented.

Such invention provides UI having the following formula: H-Asn-Asp-Asp-Pro-Pro-Ile-Ser-Ile-Asp-Leu-Thr-Phe-His-Leu-Leu-Arg-Asn-Met-Ile-Glu-Met-Ala-Arg-Asn-Glu-Asn-Gln-Arg-Glu-Gln-Ala-Gly-Leu-Asn-Arg-Lys-Tyr-Leu-Asp-Glu-Val-$NH_2$ and biologically-active fragments thereof.

Such peptides are synthesized by a suitable method, such as by exclusively solid-phase techniques, by partial solid-phase techniques, by fragment condensation or by classical solution addition. UI and certain fragments may also be synthesized by recently developed recombinant DNA techniques.

Common to chemical syntheses of peptides is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with various of these residues having side-chain protecting groups.

Also considered to be within the scope of the present invention is an intermediate having a formula such as follows: $X^1$-Asn($X^4$)-Asp($X^5$)-Asp($X^5$)-Pro-Pro-Ile-Ser($X^2$)-Ile-Asp($X^5$)-Leu-Thr($X^2$)-Phe-His($X^7$)-Leu-Leu-Arg($X^3$)-Asn($X^4$)-Met($X^8$)-Ile-Glu($X^5$)-Met($X^8$)-Ala-Arg($X^3$)-Asn($X^4$)-Glu($X^5$)-Asn($X^4$)-Gln($X^4$)-Arg($X^3$)-Glu($X^5$)-Gln($X^4$)-Ala-Gly-Leu-Asn($X^4$)-Arg($X^3$)-Lys($X^6$)-Tyr($X^9$)-Leu-Asp($X^5$)-Glu($X^5$)-Val-$X^{10}$ wherein: $X^1$ is either hydrogen or an $\alpha$-amino protecting group. The $\alpha$-amino protecting groups contemplated by $X^1$ are those known to be useful in the art in the step-wise synthesis of polypeptides. Among the classes of $\alpha$-amino protecting groups covered by $X^1$ are (1) acyl-type protecting groups, such as formyl, acrylyl(Acr), benzoyl(Bz) and acetyl(Ac) which are preferably used only at the N-terminal; (2) aromatic urethane-type protecting groups, such as benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethoxycarbonyl, isopropyloxycarbonyl, ethoxycarbonyl, allyloxycarbonyl; (4) cycloalkyl urethan-type protecting groups, such as cyclopentyloxycarbonyl, adamantyloxycarbonyl, and cyclohexyloxycarbonyl; and (5) thiourethan-type protecting groups, such as phenylthiocarbonyl. The preferred α-amino protecting group is BOC.

$X^2$ is a protecting group for the hydroxyl group of Thr and Ser and is preferably selected from the class consisting of acetyl(Ac), benzyl(Bz), tert-butyl, triphenylmethyl(trityl), tetrahydropyranyl, benzyl ether(Bzl) and 2,6-dichlorobenzyl (DCB). The most preferred protecting group is Bzl. $X^2$ can be hydrogen, which means there is no protecting group on the hydroxyl group.

$X^3$ is a protecting group for the guanidino group of Arg preferably selected from the class consisting of nitro, p-toluenesulfonyl(Tos), Z, adamantyloxycarbonyl and BOC, or is hydrogen. Tos is most preferred.

$X^4$ is hydrogen or a protecting group for the amido group of Asn or Gln and is preferably xanthyl(Xan).

$X^5$ is hydrogen or an ester-forming protecting group for the β- or γ-carboxyl group of Asp or Glu, preferably selected from the class consisting of benzyl(OBzl) 2,6-dichlorobenzyl, methyl, ethyl and t-butyl esters. Obzl is most preferred.

$X^6$ is hydrogen or a protecting group for the side chain ε-amino substituent of Lys. Illustrative of suitable side chain amino protecting groups are Z, 2-chlorobenzyloxycarbonyl(2-Cl-Z), Tos, t-amyloxycarbonyl(Aoc), BOC and aromatic or aliphatic urethan-type protecting groups as specified hereinbefore.

$X^7$ is hydrogen or a protecting group for the imidazole nitrogen of His, such as Tos or 2,4-dinitrophenyl(DNP).

$X^8$ is a protecting group for the sulfur of Met, such as oxygen, or des-$X^8$. Unprotected Met is preferred.

$X^9$ is hydrogen or a protecting group for the hydroxyl group of Tyr, such as DCB, p-methoxybenzyl or Bzl, with DCB being preferred.

The selection of a side chain amino protecting group is not critical except that it should generally be one which is not removed during deprotection of the α-amino groups during the synthesis. Hence, the α-amino protecting group and the side chain amino protecting group cannot be the same. However, Xan is an exception, as once coupling is complete, further protection of the amido group is not of prime importance.

$X^{10}$ is selected from the class consisting of NH$_2$, carboxyl protecting groups which can be cleared under conditions that do not cleave the $X^5$ group, and an anchoring bond used in solid phase synthesis for linking to a solid resin support, preferably one represented by the formulae:

—O—CH$_2$-benzyl-polyamide resin support,

—NH-benzhydrylamine (BHA) resin support, and

—NH-paramethylbenzhydrylamine (MBHA) resin support.

The polyamide polymer is commercially available and is discussed in detail in *Bioorganic Chemistry*, 8, 351–370 (1979) where a preferred version of it is discussed in connection with the synthesis illustrated in FIG. 6. When it is employed, the side-chain-protecting groups may first be cleaved by hydrogen fluoride (HF) treatment, and the peptide may subsequently be cleaved from the resin as the amide by ammonolysis. Use of BHA or MBHA resin is preferred, and cleavage directly gives the UI amide or UI fragment amide.

In the formula for the intermediate, at least one of $X^1$, $X^2$, $X^3$, $X^4$, $X^5$, $X^6$, $X^7$, $X^8$, $X^9$ and $X^{10}$ is a protecting group or an anchoring bond. In selecting a particular side chain protecting group to be used in the synthesis of the peptides, the following rules are followed: (a) the protecting group must retain its protecting properties and not be split off under coupling conditions, (b) the side-chain protecting group must be stable to the deblocking reagent and, with the exception of Xan, should also be stable under the reaction conditions selected for removing the α-amino protecting group at each step of the synthesis, and (c) the side-chain-protecting group must be removable, upon the completion of the synthesis of the desired amino acid sequence, under reaction conditions that will not alter the peptide chain. When $X^{10}$ is a protecting group at the C-terminal, it should be chosen so that it can be cleaved under conditions which will not also cleave the $X^5$ protecting group for the side-chain-carboxyl group of Asp or Glu, e.g. $X^{10}$ may be BHA or MBHA when $X^5$ is OBzl or $X^{10}$ may be OBzl when $X^5$ is t-butyl ester or H. This allows the C-terminus to be deprotected and amidated upon completion of the systhesis (by classical methods, fragment condensation or a combination thereof) without amidating the side-chain carboxyl groups, which are subsequently deprotected, except of course in the case where $X^5$ is H.

The peptides are preferably prepared using solid phase synthesis, such as that described by Merrifield, *J. Am. Chem. Soc.*, 85, p 2149 (1964), although other equivalent chemical syntheses known in the art can also be used as previously mentioned. Solid-phase synthesis is commenced from the C-terminal of the peptide by coupling a protected α-amino acid to a suitable resin as generally set forth in U.S. Pat. No. 4,244,946 issued Jan. 21, 1981 to Rivier et al., the disclosure of which is incorporated herein by reference. Such a starting material for UI peptides can be prepared by attaching α-amino-protected Val to a MBHA resin.

Val protected by BOC is coupled to the MBHA resin using methylene chloride and dimethylformamide (DMF). Following the coupling of BOC-Val to the resin support, the α-amino protecting group is removed, as by using trifluoroacetic acid(TFA) in methylene chloride, or using TFA alone or with HCl in dioxane. Preferably 50 weight % TFA in methylene chloride is used with 1–5 weight % 1,2 ethanedithiol. Deprotection is carried out at a temperature between about 0° C. and room temperature. Other standard cleaving reagents and conditions for removal of specific α-amino protecting groups may be used as described in Schroder and Lubke, "The Peptides", 1 pp 72–75 (Academic Press 1965).

After removal of the α-amino protecting group of Val, the remaining α-amino- and side-chain-protected amino acids are coupled step-wise in the desired order to obtain the intermediate compound defined hereinbefore. As an alternative to adding each amino acid separately in the synthesis, some of them may be coupled to one another prior to addition to the solid phase reactor.

The selection of an appropriate coupling reagent is within the skill of the art. Particularly suitable as a coupling reagent is N,N'-dicyclohexyl carbodiimide(DCCI).

The activating reagents used in the solid phase synthesis of the peptides are well known in the peptide art. Examples of suitable activating reagents are carbodiimides, such as N,N'-diisopropyl carbodiimide and N-ethyl-N'-(3-dimethylaminopropyl)carbodiimide. Other activating reagents and their use in peptide coupling are described by Schroder and Lubke, supra, in Chapter III and by Kapoor, *J. Phar. Sci.*, 59, pp 1–27 (1970).

Each protected amino acid or amino acid sequence is introduced into the solid phase reactor in about a four-fold excess, and the coupling is carried out in a medium of dimethylformamide(DMF):$CH_2Cl_2$ (1:1) or in DMF or $CH_2Cl_2$ alone. In instances where the coupling is carried out manually, the success of the coupling reaction at each stage of the synthesis is monitored by the ninhydrin reaction, as described by E. Kaiser et al., *Anal. Biochem.* 34, 595 (1970). In cases where incomplete coupling occurs, the coupling procedure is repeated before removal of the α-amino protecting group prior to the coupling of the next amino acid. The coupling reactions can be performed automatically, as on a Beckman 990 automatic synthesizer, using a program such as that reported in Rivier et al., *Biopolymers*, 1978, 17, pp.1927–1938.

After the desired amino acid sequence has been completed, the intermediate peptide is removed from the resin support by treatment with a reagent, such as liquid hydrogen fluoride. Selection of the all of the protecting groups is preferably such that HF treatment not only cleaves the peptide from the resin but also cleaves all remaining side-chain-protecting groups $X^2$, $X^3$, $X^4$, $X^5$, $X^6$, $X^7$, $X^8$ and $X^9$ and the α-amino protecting group $X^1$ to obtain the peptide, and in this respect, the BOC group is preferred. When using hydrogen fluoride for cleaving, anisole and methylethyl sulfide are included in the reaction vessel as scavengers. Because Met is present in the sequence, the BOC protecting group is preferably cleaved with TFA/ethanedithiol prior to cleaving the peptide from the resin to eliminate potential S-alkylation.

The following Example sets forth a method for synthesizing UI by the solid-phase technique.

EXAMPLE I

The synthesis of UI having the formula: H-Asn-Asp-Asp-Pro-Pro-Ile-Ser-Ile-Asp-Leu-Thr-Phe-His-Leu-Leu-Arg-Asn-Met-Ile-Glu-Met-Ala-Arg-Asn-Glu-Asn-Gln-Arg-Glu-Glu-Ala-Gly-Leu-Asn-Arg-Lys-Tyr-Leu-Asp-Glu-Val-$NH_2$ is conducted in a stepwise manner on a paramethylbenzhydrylamine hydrochloride resin, such as available from Bachem, Inc., having a substitution range of about 0.1 to 0.5 mmoles/gm. resin. The synthesis is performed on an automatic Beckman 990A peptide synthesizer. Coupling of BOC-Val results in the substitution of about 0.35 mmol. Val per gram of resin. All solvents that are used are carefully degassed, preferably by sparging with an inert gas, e.g. helium or nitrogen, to insure the absence of oxygen that might undesirably oxidize the sulfur of the Met residue.

After deprotection and neutralization, the peptide chain is built step-by-step on the resin. Generally, one to two mmol. of BOC-protected amino acid in methylene chloride is used per gram of resin, plus one equivalent of 1 molar DCCI in methylene chloride, for two hours.

When BOC-Arg(Tos) is being coupled, a mixture of 50% DMF and methylene chloride is used. Bzl is used as the hydroxyl side-chain protecting group for Ser and Thr. P-nitrophenyl ester(ONp) is used to activate the carboxyl end of Asn or Gln, and for example, BOC-Asn(ONp) is coupled overnight using one equivalent of HOBt in a 50% mixture of DMF and methylene chloride. The amido group of Asn or Gln is protected by Xan when DCC coupling is used instead of the active ester method. 2-Cl-Z is used as the protecting group for the Lys side chain, and Tyr is protected by DCB. Tos is used to protect the guanidino group of Arg and the imidazole group of His, and the side chain carboxyl group of Glu or Asp is protected by OBzl. Met is left unprotected. At the end of the synthesis, the following composition is obtained BOC-Asn(Xan)-Asp(OBzl)-Asp(OBzl)-Pro-Pro-Ile-Ser(Bzl)-Ile-Asp(OBzl)-Leu-Thr(Bzl)-Phe-His(Tos)-Leu-Leu-Arg(Tos)-Asn(Xan)-Met-Ile-Glu(OBzl)-Met-Ala-Arg(Tos)-Asn(Xan)-Glu(OBzl)-Asn(Xan)-Gln(Xan)-Arg(Tos)-Glu(OBzl)-Gln(Xan)-Gln(Xan)-Ala-Gly-Leu-Asn(Xan)- rg(Tos)-Lys(2-Cl-Z)-Tyr(DCB)-Leu-Asp(OBzl)-Glu(OBzl)-Val-resin support. Xan may have been partially or totally removed by TFA treatment used to deblock the α-amino protecting group.

In order to cleave and deprotect the resulting protected peptide-resin, it is treated with 1.5 ml. anisole, 0.5 ml. of methylethylsulfide and 15 ml. hydrogen fluoride (HF) per gram of peptide-resin, first at −20° C. for 20 min. and then at 0.° C. for one-half hour. After elimination of the HF under high vacuum, the resin-peptide is washed alternately with dry diethyl ether and chloroform, and the peptides are then extracted with degassed 2N aqueous acetic acid and separated from the resin by filtration. The peptide is purified by gel permeation followed by semi-preparative HPLC as described in Marki et al., *J. of Amer. Chem. Soc.*, 103, 3178–3185 (1981) or by preparative HPLC for large-scale purification.

To produce the fragment carp UI (4-41), the synthesis is repeated, with the exception that the last three residues, i.e. Asp, Asp and Asn, are not added. Alternatively, the peptide can be generated from UI (1-41) by mild acid hydrolysis.

EXAMPLE II

UI was extracted, isolated and purified in the following manner. About 4,000 urophyses dissected from *Cyprinus carpio* were dehydrated in acetone and homogenized in 0.1N HCl, heated for 15 minutes in a boiling water bath, centrifuged at 3,000 rpm for 20 minutes, and the supernatant was analyzed by gel exclusion chromatography on a Biogel P-6 column (2.6×90 cm) using 0.1N HCl as eluant. Bioactive fractions were pooled and further purified by ion exchange chromatography on a sulfopropyl(SP)-Sephadex C-25 column (1.6×70 cm) using two acetic acid/pyridine acetate gradients at 5° C. The first gradient was initiated from 0.1N acetic acid to 0.2N pyridine acetate, pH 4.8, and the second was from the latter to 2.0N pyridine acetate, ph 6.5. Bioactive fractions were again pooled and lyophilized, and aliquots were further purified by reverse phase HPLC on a Spectra-Physics SP 8000 liquid chromatograph equipped with an RP-8 column (Brownlee Lab), using a linear 19-min gradient of 10–55% acetonitrile in 0.2M ammonium acetate buffer, ph 4.0, at a flow rate of 1.5 ml/min at 40° C.

A portion of the peptide was hydrolyzed in sealed evacuated tubes containing 4N methanesulfonic acid and 0.2% tryptamine for 24 hours at 110° C. Amino acid analyses of the hydrolysates using a Beckman 121 MB amino acid analyzer showed the following amino acid ratios: Asx(5.97), Thr(1.05), Ser(1.13), Glx(6.18), Pro(1.87), Gly(1.18), Ala(2.10), Val(0.76), Met(2.01), Ile(3.09), Leu(5.29), Tyr(0.97), Phe(0.96), Lys(0.94), His(1.08) and Arg(4.19) which indicated that a 38-residue peptide was isolated. Characterization showed it to have the sequence herein before indicated for UI (4-41).

EXAMPLE III

The procedure of Example II was repeated, leaving out the step of heating in 0.1N HCl using the boiling water bath and instead extracting for a longer period of time in cold 0.1N HCl.

Lyophilized active zones from the HPLC were used for composition and structural analysis which gave the following 41-residue sequence which is carp UI: H-Asn-Asp-Asp-Pro-Pro-Ile-Ser-Ile-Asp-Leu-Thr-Phe-His-Leu-Leu-Arg-Asn-Met-Ile-Glu-Met-Ala-Arg-Asn-Glu-Asn-Gln-Arg-Glu-Gln-Ala-Gly-Leu-Asn-Arg-Lys-Tyr-Leu-Asp-Glu-Val-$NH_2$.

EXAMPLE IV

The urotensin peptides from Example II and III are examined for effects on the secretion of ACTH and $\beta$-endorphin in vitro and also examined in vivo. A high potency of these two peptides to stimulate the secretion of ACTH and $\beta$-endorphin by cultured rat pituitary cells is observed, substantially indistinguishable from each other and comparable to amunine (CRF). The peptides also stimulate ACTH and $\beta$-END-LI secretion in vivo in several rat preparations. UI activity of the peptides was measured by the isolated rat hind limb assay, Lederis, K. et al. "Effects and Assay of Urotensin I on the Perfused Hind Limb of the Rat." *Gen. Comp. Endocrinol.*, 24:10–16, 1974. In vivo hypotensive activity of extracted peptides was measured in anaesthetized rats, Lederis, K. and Medakovic, M. "Pharmacological Observations on the Hypotensive Action of Extracts of Teleost Fish Urophyses (Urotensin I) in the Rat." *Br. J. Pharmacol.* 51:315–324, 1974, and in anaesthetized dogs, MacCannell and Lederis, "Dilatation of the Mesenteric Vascular Bed of the Dog Produced by a Peptide, Urotensin I." *J. Pharm. Exp. Ther.* 203:38–46, 1977. In the dog and monkey, both peptides, urotensin I and urotensin I (4-41) produce a modest but sustained depression of the blood pressure which appears to be due solely to dilatation of the mesenteric vascular bed; neither peptide dilates other vascular beds. Both peptides also cause a more marked fall in blood pressure in the rat, where vascular dilatation appears to be less selective. The peptides are several times more potent than amunine in stimulating the secretion of ACTH by teleost fish pituitaries.

In the pentobarbital-anaesthetized dog, the threshold dose of UI for mesenteric vasodilatation, when given close arterially into the cephalic mesenteric A, is between 0.001 and 0.01 µg for both carp UI (1-41) and for the 4-41 fragment of carp UI. Doses of 0.1–0.5 µg of both peptides produce a 50-150% increase in mesenteric flow; accompanying changes in blood pressure are very modest (about 10% decrease). The two synthetic peptides described above have been found to be equipotent with the extracted and purified peptides, as tested in the anaesthetized dog in vivo and in the isolated rat hind limb, as described above, as well when tested in isolated mesenteric artery strips of the rat according to Muramatsu, I., Miura, A., Fujiwara, M. and Lederis, K., *Gen. Comp. Endocrinol.* 45:446-452, 1981. Comparison of the two extracted and the two synthetic carp peptides indicated that synthetic UI(1-41) had 119±19% activity and synthetic UI (4-41) had 123±58% activity of the activity of the respective extracted carp UI peptides.

Carp UI and its biologically active fragments are expected to be very useful in the following clinical conditions:

(a) mesenteric ischemia (ischemic bowel syndrome, ischemic intestinal ulceration, ischemic colitis, ischemic proctitis, nonocclusive mesenteric vascular ischemia, intestinal angina, and mesenteric angina vasculitis) as well as other situations where the blood supply to the intestine is compromised;

(b) anastomotic gut surgery—to increase blood supply to the suture line and thus promote healing;

(c) shock and hypotension, such as may occur with trauma, hemorrhage, fluid loss, infection or may be due to cardiac causes—there being reasonable evidence that decreased intestinal blood flow is involved in the genesis or maintenance of all types of hypotension and shock; and (d) heart failure and other cardiac conditions where a reduction in the "load" against which the heart has to pump is desirable, sometimes termed afterload reduction. (Existing vasodilator drugs may excessively decrease filling of the heart so that cardiac output falls, whereas a selective mesentric vasodilator drug would not.)

Carp UI is also expected to be of value in the following clinical conditions: inflammatory bowel disease, such as Crohn's (regional ileitis and granulomatous colitis), and ulcerative colitis; and hypertension from various causes, including portal hypertension, which is commonly treated by administration of vasopressin, which is released endogenously by these UI peptides.

If these UI peptides gain access to the brain, they should have significant effects on the brain as a mediator or limiter of the body's stress response—ACTH and $\beta$-END secretion being a "sine qua non" of an animal's response. Because they elevate the levels of ACTH and $\beta$-END, administration can be used to induce their effects on the brain and its periphery to thereby influence memory, mood, pain appreciation, etc., and more specifically, alertness, depression and/or anxiety.

UI or its fragment, or nontoxic addition salts of either, combined with a pharmaceutically acceptable carrier to form a pharmaceutical composition, may be administered to mammals, including humans, either intravenously, subcutaneously, intramuscularly, percutaneously, intracerebrospinally or even orally (when suitable oral carriers are developed). The peptides shoud be at least about 93% pure and preferably should have a purity of at least about 98%. This purity means that the intended peptide constitutes the stated weight % of all like peptides and peptide fragments present. Their administration may be employed by a physician to lower blood pressure or to alter regional blood flow, and the required dosage will vary with the particular condition being treated, with the severity of the condition and with the duration of desired treatment.

Such peptides are often administered in the form of pharmaceutically acceptable nontoxic salts, such as acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, sulphate, phosphate, tannate, pamoate, oxalate, fumarate, gluconate, alginate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered under the guidance of a physician, and pharmaceutical compositions will usually contain the peptide in conjunction with a conventional, pharmaceutically-acceptable carrier. Usually, the dosage will be from about 0.01 to about 200 micrograms of the peptide per kilogram of the body weight of the host. In some instances, treatment of subjects with these peptides can be carried out in lieu of the administration of ACTH or corticosteroids, and in such instances, a dosage as low as about 10 ng/Kg of body weight may be employed. As used herein all temperatures are °C. and all ratios are by volume. Percentages of liquid materials are also by volume.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, substitutions and modifications in the UI peptide chain can be made in accordance with present or future developments without detracting from the potency, and such resultant peptides are considered as being within the scope of the invention. Moreover, the fragment of the peptide extending from Pro-Pro near the N-terminal to Asn-Gln-Arg (UI 4-28) has also been found to be biologically active.

Various features of the invention are emphasized in the claims which follow.

We claim:

1. A synthetic polypeptide having the formula: H-Asn-Asp-Asp-Pro-Pro-Ile-Ser-Ile-Asp-Leu-Thr-Phe-His-Leu-Leu-Arg-Asn-Met-Ile-Glu-Met-Ala-Arg-Asn-Glu-Asn-Gln-Arg-Glu-Gln-Ala-Gly-Leu-Asn-Arg-Lys-Tyr-Leu-Asp-Glu-Val-NH$_2$ or a biologically active peptide fragment thereof containing at least the residues in positions 4 through 28; or a nontoxic addition salt of either.

2. A compound in accordance with claim 1 wherein said peptide has the formula: H-Pro-Pro-Ile-Ser-Ile-Asp-Leu-Thr-Phe-His-Leu-Leu-Arg-Asn-Met-Ile-Glu-Met-Ala-Arg-Asn-Glu-Asn-Gln-Arg-Glu-Gln-Ala-Gly-Leu-Asn-Arg-Lys-Tyr-Leu-Asp-Glu-Val-NH$_2$.

3. A pharmaceutical composition for increasing intestinal blood flow and lowering blood pressure in mammals comprising an effective amount of a peptide in accordance with claim 1 and a pharmaceutically acceptable liquid or solid carrier therefor.

4. A method for increasing intestinal blood flow and lowering the blood pressure of a mammal, which method comprises administering to said mammal an effective amount of a pharmaceutical composition as set forth in claim 3.

5. A method in accordance with claim 4 wherein said administering is carried out either intravenously, subcutaneously, precutaneously, intracerebrospinally or intramuscularly.

6. A method of elevating the secretion of ACTH and corticosteroids which comprises administering an effective amount of the peptide of claim 1.

7. A method of elevating the secretion of β-END, which comprises administering an effective amount of the peptide of claim 1.

8. A method of elevating the secretion of ACTH and corticosteroids which comprises administering an effective amount of the peptide of claim 2.

9. A method of elevating the secretion of β-END, which comprises administering an effective amount of the peptide of claim 2.

* * * * *

UNITED STATES PATENT AND TRADEMARK OFFICE
CERTIFICATE OF CORRECTION

PATENT NO. : 4,533,654

DATED : August 6, 1985

INVENTOR(S) : Lederis et al.

It is certified that error appears in the above-identified patent and that said Letters Patent is hereby corrected as shown below:

Title page:

Add --Jean E. F. Rivier, La Jolla, California-- as Inventor.

Column 3, Line 30, change "Obzl" to --OBzl--.

Column 5, Line 52, change "Gln-Arg-Glu-Glu" to
   --Gln-Arg-Glu-Gln--.

Column 6, Line 21, change "rg(Tos)" to --Arg(Tos)--.

Column 8, Line 57, correct the spelling of --should--.

Signed and Sealed this

Seventeenth Day of December 1985

[SEAL]

Attest:

DONALD J. QUIGG

Attesting Officer

Commissioner of Patents and Trademarks